(12) United States Patent
Taylor et al.

(10) Patent No.: US 7,188,382 B1
(45) Date of Patent: Mar. 13, 2007

(54) ANKLE BOLSTER

(76) Inventors: Eleanor L. Taylor, 6612 Manor Hill Rd., San Antonio, TX (US) 78257;
William Gregory Taylor, 6612 Manor Hill Rd., San Antonio, TX (US) 78257

(*) Notice: Subject to any disclaimer, the term of this patent is extended or adjusted under 35 U.S.C. 154(b) by 76 days.

(21) Appl. No.: 11/010,655

(22) Filed: Dec. 13, 2004

(51) Int. Cl.
*A61G 7/075* (2006.01)
(52) U.S. Cl. ............... 5/648; 5/652; 5/655.9; 128/882
(58) Field of Classification Search ......... 5/630, 5/648, 652, 655.9; 128/877, 878, 882
See application file for complete search history.

(56) References Cited

U.S. PATENT DOCUMENTS

| | | | | | |
|---|---|---|---|---|---|
| 3,903,878 | A | * | 9/1975 | Spann | 302/21 |
| 4,982,745 | A | * | 1/1991 | Shields | 128/877 |
| 5,839,139 | A | * | 11/1998 | Fink | 5/648 |
| 6,186,967 | B1 | * | 2/2001 | Messina | 602/23 |

* cited by examiner

*Primary Examiner*—Michael Trettel

(57) ABSTRACT

This device is made to protect the bony surfaces of a foot from prolonged pressure and ultimate skin breakdown. It consists of a cylinder of dense foam that is fitted to encompass the lower leg of a user from the knee to the ankle. When in place on the leg a of a user lying in bed, it will support the lower leg such that the foot will not be in contact with the firm surface of the bed, thus providing total pressure relief to the foot. The user can also lie in any position, even prone, with out interference from this device.

6 Claims, 2 Drawing Sheets

Fig. 3

ANKLE BOLSTER

BACKGROUND OF THE INVENTION

1) Field of the Invention

This invention relates to a specific device designed to help prevent pressure sores on ankles and heels of bedridden persons.

2) Description of Prior Art

Decubitus ulcers are a common complication of prolonged confinement to bed. Many persons who are confined to bed do not change position frequently enough to prevent the sustained pressure over bony prominences that leads to skin breakdown and pressure sores. The causes of this immobility are usually paralysis, or coma, or a simple lack of adequate sensation in the extremities. These people need frequent repositioning to prevent pressure sores.

Over the years several devices have been used to help in positioning. Some devices are essentially large pads that surround the feet. These are made of several different materials, i.e. foam, cotton, water bags, air bags, etc. Their design is to displace the concentrated pressure from a bony point, to a larger area of the foot. These do relieve a percentage of the pressure to the bony areas, but not all, and will eventually lead to skin breakdown because they provide some continuous pressure to the areas at risk. Some devices are made of hard rigid materials with gaps over the heels and lined with soft material. These displace the pressure halfway up the calf and off the heel, but generally do not protect the ankles. They are also heavy and bulky and not well suited to a person lying in any position other than completely supine. When the user is lying on the side, the boots do not lie flat without putting excess weight on the ankles; and the user cannot lie prone without twisting the legs. Another device is a large block of foam with holes cut out for heel and ankles. These are unwieldy because they force the foot to lie straight up and down or flat on the side. They extend just above the ankle and frequently migrate off the foot, leaving it to lie on a firm surface. One device has similarities to the current invention in that it supports an arm or a leg and can roll. That device does not support the entire leg but puts the full weight of the lower leg on a narrow zone just above the ankle. Placing the foot or hand in an exaggerated elevated position is not ergonomic or comfortable, but effective in reducing swelling, yet has no advantage over level positioning in preventing pressure sores.

BRIEF SUMMARY OF THE INVENTION

This application provides for a leg support that allows the foot to rest free from any pressure when the user is lying in bed. This is a cylinder of moderately dense foam that fits on the user from the ankle to the knee. The inner tunnel of the cylinder is tapered with a smaller inside diameter at the ankle than at the knee; so that it will fit closely at both ends. The inner side may have an additional very soft thin foam layer for increased comfort. The outer side should be firm enough to keep the foot off the bed without collapsing under the weight of the leg. The cylinder is open along the side, in a zig-zag fashion, to allow easy application to the user's leg; and this opening is held closed with securing straps with hook and loop fasteners.

DETAILED DESCRIPTION OF THE INVENTION

Figure 1:
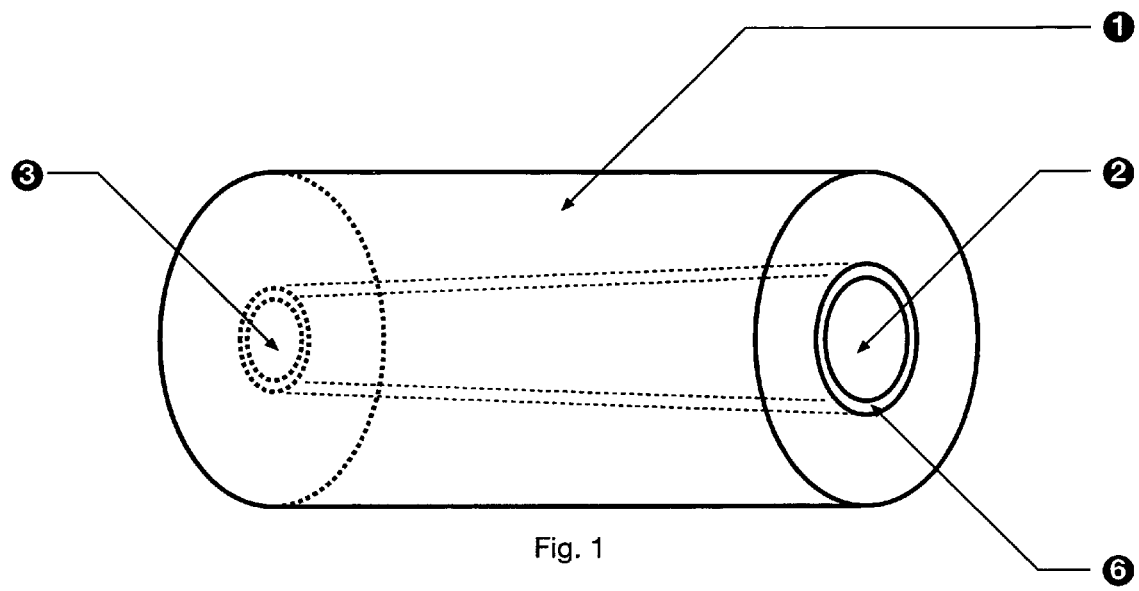
FIG. 1 is a view of the cylinder (1) showing the larger opening (2) at one end and a smaller opening (3) at the other end.
Figure 2:
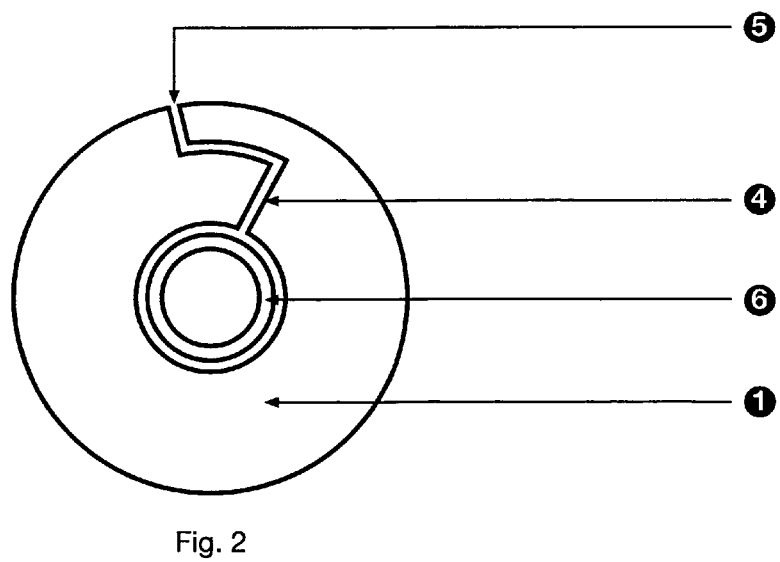
FIG. 2 is an end view of the cylinder (1) showing flanged arrangement (4) of the side opening (5), the soft inner lining (6) inside the cylinder.
Figure 3:
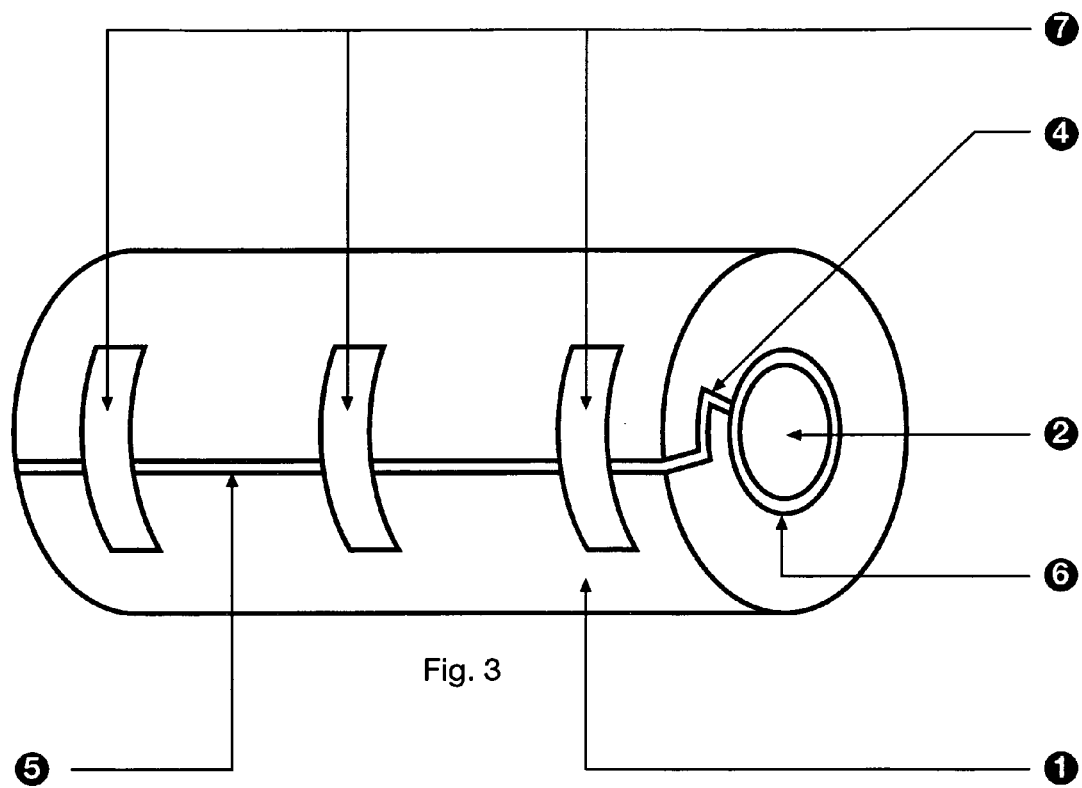
FIG. 3 is a side view of the cylinder (1) showing the larger opening (2) at one end, the side opening (5), and the securing straps (7).

The object of this invention is to provide a device that continuously supports the leg of the user when confined to bed in such a manner that the bony prominences of the foot are not subjected to any pressure from the bed, thus preventing decubitus ulcers. With reference to FIGS. 1–3, it is seen that the device consists of a cylinder of foam rubber, or other material of like function, that is long enough to reach from the user's ankle to knee. It is also evident that the cylinder has inner (1) and outer (2) surfaces, such that the inner tunnel is tapered, being narrower at the ankle end and wider at the knee end, to allow for comfortable fitting to the user's leg without being excessively loose or tight at either end. The inner surface can also be supplied with a soft inner layer for increased comfort. It is also seen that the outer diameter of the cylinder is sufficient to support the leg high enough off the bed to prevent the foot from resting on the bed. The cylinder is opened along the side (3) to allow easy application to the user's leg. The opening is made in such a way that there are overlapping flanges (4) on each side that fit together on application thus preventing one side from overrunning the other which would lead to a lumpy, irregular closure. The cylinder is secured in a closed position by overlapping closure material with hook and loop fasteners. The cylinder can be made in different sizes for different size users; and finer adjustments can be made by trimming material off one open edge to make the cylinder smaller without changing its functional characteristics.

We claim:

1. A supporting device for a lower leg and foot comprising;

A cylinder made of dense foam, having an inner surface and an outer surface, wherein the inner surface of the device is in contact with the leg of the user between the knee and the ankle, and tapered to accommodate the differing diameters of the user's calf and ankle, and the outer surface of the device is in contact with the surface upon which the user is lying, and the total thickness of the device is constant from one end to the other, and sufficient to suspend the foot off the surface upon which the user and device are lying.

2. The device according to claim 1, wherein the inner surface of the device may be fitted with an extra layer of soft material for comfort.

3. The device according to claim 1, is open along the entire length of the cylinder such that the adjacent edges of this opening form two flanges that overlap and are secured to each other with hook and loop fasteners.

4. The device according to claim 1, wherein the outer surface of the cylinder is also tubular and can roll in a full circle with no restriction from the device.

5. The device according to claim 1, wherein the cylinder can be cut to size in length and in circumference to accommodate different size users.

6. The device according to claim 1, wherein the user's leg is supported from the knee to the ankle parallel to the surface upon which the user is lying and elevated just high enough to relieve pressure on the foot from contact with the lying surface.

* * * * *